United States Patent [19]

Inagaki et al.

[11] Patent Number: 5,994,423
[45] Date of Patent: Nov. 30, 1999

[54] URINE ABSORBER, METHOD FOR PRODUCING IT, URINE ABSORBING METHOD UTILIZING IT AND PORTABLE TOILET

[75] Inventors: Yasuhito Inagaki; Kazuki Satake, both of Kanagawa, Japan

[73] Assignee: Sony Corporation, Tokyo, Japan

[21] Appl. No.: 09/166,893

[22] Filed: Oct. 6, 1998

[30] Foreign Application Priority Data

Oct. 6, 1997 [JP] Japan .................................. 09-273077
Mar. 4, 1998 [JP] Japan .................................. 10-052497

[51] Int. Cl.$^6$ ...................................................... C08J 9/00
[52] U.S. Cl. .......................... 521/146; 521/134; 521/138; 521/139; 521/147; 521/148; 521/180; 521/182; 521/189; 604/358; 604/369

[58] Field of Search ..................................... 521/146, 147, 521/148, 180, 182, 189, 134, 138, 139

[56] References Cited

U.S. PATENT DOCUMENTS

| 4,529,739 | 7/1985 | Scott et al. | 521/72 |
| 4,808,637 | 2/1989 | Boardmaw et al. | 521/50.5 |
| 4,990,541 | 2/1991 | Nielsen et al. | 521/70 |

*Primary Examiner*—Morton Foelak
*Attorney, Agent, or Firm*—Hill & Simpson

[57] ABSTRACT

A urine absorber superior in smell extinguishing and urine absorption properties and in absorption stability is to be prepared. To this end, a polymer of styrene and/or conjugate diene and acrylonitrile, containing a predetermined amount of a sulfonide and/or its salts, is used as the urine absorber.

2 Claims, No Drawings

URINE ABSORBER, METHOD FOR PRODUCING IT, URINE ABSORBING METHOD UTILIZING IT AND PORTABLE TOILET

BACKGROUND OF THE INVENTION

1. Field of the Invention

This invention relates to a urine absorber employing a hydrophilic resin exhibiting superior absorption and smell extinguishing properties for urine of the human being and animals, and a method for producing the urine absorber.

2. Description of the Related Art

With the recent pet boom, chromatic road stagnation and an increased number of aged persons bound to the beds, there is an increasing demand for a urine absorber capable of recovering urine of the human being or animals at an arbitrary place. It is noted that the site of use of the urine absorber is mostly a more or less sealed space, such as pet room, a moving vehicle or an indoor bedroom.

For this reason, suitable measures for combatting the small emitted from the urine are crucial. The current technique is not satisfactory such that a portable toilet employing a higher smell extinguishing effect has been a desideratum. On the other hand, the current technique also is not satisfactory as to the power of urine absorption. Moreover, there is raised a problem as to coloration and lack in water retentivity on absorbing the urine by the urine absorber, specifically, urine backflow from the absorber. Therefore, a suitable technique for combatting smell extinguishing properties, urine absorption properties, water retentivity or coloration has also been a desideratum.

SUMMARY OF THE INVENTION

It is therefore an object of the present invention to provide a urine absorber, having superior smell extinguishing effects, a method for producing the urine absorber and a urine absorbing method superior in urine absorption properties, water retentivity or coloration.

It is another object of the present invention to provide a portable toilet employing the improved urine absorber.

As a result of our perseverant researches towards accomplishing the above objects, the present inventors have found that a urine absorber comprising a hydrophilic resin wherein, in a polymer having sulfonic acid groups and/or sulfonate groups as constituent units, there are contained the aforementioned sulfonic acid groups and/or sulfonate groups in an amount corresponding to 2 to 95 mol % of the entire constituent units, can be used as a urine absorber to overcome the problems inherent in the current urine absorber, that is urine absorbing properties, smell extinguishing properties, water retention stability or coloration. This finding has led to the present invention concerning the urine absorber and its manufacturing method.

That is, the urine absorber according to the present invention is comprised of a hydrophilic resin containing sulfonic acid groups and/or sulfonate groups in a polymer in an amount of 2 to 95 mol % and preferably 10 to 70 mol % based on the entire constituent units.

The hydrophilic resin may be a sulfonide of a polymer containing at least one of styrene or conjugated diene in an amount corresponding to 5 to 95 mol % and preferably 40 to 80 mol % of the entire constituent units.

The hydrophilic resin may also be a sulfonide of a polymer containing acrylonitrile units in addition to the styrene and conjugate diene units in an amount corresponding to 5 to 95 mol % and preferably 10 to 50 mol % to the entire constituent units, or salts thereof.

The hydrophilic resin may also be is a sulfonide of at least one of an acrylonitrile-butadiene-styrene resin, a styrene-acrylonitrile copolymer resin and acrylonitrile-butadiene rubber, and/or salts thereof The hydrophilic resin may also be a sulfonide of a used-up waste material and/or salts thereof.

It is possible for at least one of carbon black and titanium oxide to be contained in an amount of 0.01 to 20 wt % and preferably 0.05 to 10 wt % in the hydrophilic resin.

A method for preparing a urine absorber according to the present invention includes the steps of sulfonating a polymer containing sulfonic acid groups and/or sulfonate groups in an amount corresponding to 2 to 95 mol % of entire constituent units by a sulfonizing agent to give a sulfonated reaction mass and washing and drying the sulfonated reaction mass to give a hydrophilic resin.

A urine absorbing method employing the above urine absorber includes contacting the urine absorber with urine to adsorb and remove the urine.

A portable toilet employing the urine absorber contains the urine absorber in a bag to absorb the urine contacted with the bag.

The present invention thus provides a urine absorber superior in urine absorption and smell extinguishing properties and in water retention stability to resolve the problem of coloration on urine absorption.

Since the urine absorber can be manufactured from used-up waste plastic materials, it helps utilize resources effectively to contribute to maintenance of the global environment.

DESCRIPTION OF THE PREFERRED EMBODIMENTS

The present invention will now be explained in detail.

The hydrophilic resin used as the urine absorber of the present invention contains 2 to 95 mol % and preferably 10 to 70 mol % of sulfonic acid groups or sulfonate groups. If the amount of the above groups is lower than the above specified range, the effect of capturing ammonia gases discharged from the urine or the urine absorbing effect is drastically lowered. If conversely the amount of the above groups is larger than the above specified range, the resin is dissolved in urine and liquefied such that it cannot exhibit properties as absorber.

According to the present invention, the following polymers are sulfonated to give a hydrophilic resin.

The polymer is preferably a sulfonate of a polymer containing 5 to 95 mol % and preferable 40 to 80 mol % of at least one of units of styrene or conjugate diene (butadiene or isoprene). The styrene and conjugate diene are required to introduce sulfone groups into the polymer. If the content of the two monomers is lower than the above range, the rate of introduction of the sulfone groups into the polymer is low so that the effect of capturing the ammonia gas discharged from the urine is significantly lowered. If conversely the monomer content is higher than the above range, the monomers are dissolved in water or urine.

It is desirable for the polymer to contain 2 to 95 mol % and preferably 10 to 50 mol % of acrylonitrile units in addition to the above styrene and conjugated diene. It is noted that acrylonitrile is partially hydrolyzed after the sulfonating reaction to form amide groups, which in turn contribute to improved urine absorbing properties (swelling properties). If the content of acrylonitrile in the polymer is small, the polymer is dissolved in urine after the sulfonating reaction to detract from the properties of the urine absorbing resin. If the acrylonitrile content is increased, the rate of introduction of the sulfone groups into the polymer is lowered, thus significantly lowering the adsorption and absorption ratio of ammonia or water in the urine.

If predetermined amounts of styrene, conjugated diene and acrylonitrile are contained in the polymer, it is possible for other constituent units to be contained n the waste resin material.

Examples of these other constituent units include maleic anhydride, itaconic anhydride, α-methyl styrene, acryl amide, methacrylamide, acrylic acid, methacrylic acid, acrylic acid or methacrylic acid esters (saturated or unsaturated hydrocarbons with 1 to 10 carbon atoms) vinyl acetate, vinyl chloride, ethylene, propylene, butylene, pyridine and N-vinyl pyrrolidone.

Examples of these polymers preferably include acrylonitrile-butadiene-styrene (ABS) resin, styrene-acrylonitrile (SAN) resin and acrylonitrile-butadiene rubber (NBR).

The molecular weight of the polymer (Mw) is preferably not less than 2000 in terms of the weight average molecular weight (Mw).

If the molecular weight is lower than the above range, the polymer is water-soluble after sulfonation, so that it cannot display the effect as the absorber.

Although the polymer may be a virgin material, used-up materials, (waste materials) may be used. Examples of preferred waste resin materials include those of ABS, SAN or ACS resins. These waste resin materials may be acquired from electric appliances, cars, stationery goods, measuring instruments or building materials from factories, retail stores or households.

The waste materials from factories are preferred to those from homes since the former are more uniform in composition.

These used-up materials are preferably used as starting materials in view of saving of resources and reducing the quantity of wastes.

The polymer may be alloys with other resins and may contain additives, such as pigments, dyes, stabilizers, combustion retardants, plasticizers, fillers or auxiliary agents.

It is also possible to use the used-up waste materials mixed with a virgin material.

The other resins that can be mixed with the polymers are preferably those which do not obstruct sulfonation according to the present invention. Examples of these resins include polyphenylene ether, polycarbonates, polyphenylene sulfides, polyethylene terephthalates and polybutylene terephthalates.

These resins are preferably contained in an amount not larger than 60 wt %. If the amount of theses resins exceeds 60 wt %, it becomes difficult to introduce sulfone groups into the polymer.

The polymers are preferably processed into small pieces prior to sulfonation. The following methods may be used for processing the polymer into small pieces:
(1) Crushing by a crusher followed by sieving.
Since the resin contains rubber components, the resin is preferably crushed after freezing.
(2) Heat-melting followed by pelletization to small beads.
The size of the small pieces is preferably not larger than 3.5 mesh.

If the size is larger than the above value, the reaction material is reduced in surface area such that the waste resin material can hardly be sulfonated. The result is prolonged reaction time which is not practical. Moreover, the material is lowered in absorption properties with respect to urine.

If inorganic material (carbon black and titanium oxide) is contained in the hydrophilic resin used in the urine absorber of the present invention, the urine absorber is improved further in its smell extinguishing effects. The carbon black or titanium oxide may be inherently contained in the polymer or individually added and mixed to the hydrophilic resin.

The carbon black or titanium oxide may be those routinely used as colorants for plasticizers, reinforcing agents or electrically conductivity according agents.

The carbon black may be produced by a channel method, a furnace method or a thermal method, whichever is desired. These methods may be used alone or in combination. The average particle size is 5 to 500 $\mu$m and preferably 10 to 50 $\mu$m.

It is noted that titanium oxide may be of a rutile, anatase or micro-particulate titanium type, whichever is desired. These types of titanium oxide may be used alone or in combination. The average particle size is 0.01 to 50 $\mu$m and preferably 0.05 to 10 $\mu$m. The average particle size is 0.01 to 50 $\mu$m and preferably 0.05 to 10 $\mu$m.

The content of the carbon black or titanium oxide contained in the hydrophilic resin used as the urine absorber is 0.01 to 20 wt % and preferably 0.1 to 10 wt % based on the dry weight prior to absorption into urine.

It is noted that the carbon black has the effect of physically absorbing molecules responsible for smell, while titanium oxide has the effect of dissolving smell components by light irradiation. The result is that, if carbon black or titanium oxide is contained in the hydrophilic resin, significant smell extinguishing effects are displayed.

It is also noted that the carbon black or titanium oxide ma be contained from the outset in the starting polymer or may be added to the polymer in the course of the sulfonating reaction.

According to the present invention, the polymer is converted into the hydrophilic resin by sulfonation.

Among the agents used for sulfonation, there are sulfonating agents, such as concentrated sulfuric acid, sulfuric anhydride, fuming sulfuric acid or chlorosulfonic acid.

These sulfonating agents may be used alone, in combination or in succession.

For example, the above polymer may be first processed with concentrated sulfuric acid and sulfuric anhydride may then be added to the reaction system to give the hydrophilic resin.

Although the sulfonating reaction may be carried out in a sulfonating agent, it may be carried out in a system employing an organic solvent. Among usable organic solvents, there are C1 to C2 aliphatic halogenated hydrocarbons, preferably 1,2-dichloroethane, chloroform, dichloromethane or 1,1-dichloroethane, alicyclic hydrocarbons, preferably cyclohexane, methyl cyclohexane or cyclopentane, nitro methane, nitrobenzene or sulfur dioxide, C1 to C7 paraffinic hydrocarbons, acetonitrile, carbon disulfide, tetrahydrofuran, tetrahydropyrane, 1,2-dimethoxy ethane, acetone, methylethylketone and thiophen. Preferred are C1 and C2 aliphatic halogenated hydrocarbons, alicyclic hydrocarbons, nitro methane, nitrobenzene and sulfur dioxide. There is no particular limitation to the mixing ratio of the above solvents.

For sulfonation, Louis bases may be used, if so required. Among the Louis bases, there are alkyl phosphates (triethyl phosphates or trimethyl phosphates), dioxane, acetic anhydride, ethyl acetate, ethyl palmitate, diethyl ether and dioxane.

The sulfonating agents or solvents, once used for the sulfonating reaction, may be recovered after the end of the reaction and re-used for the reaction directly or after recovery by the method of extraction or distillation.

According to the present invention, the above-mentioned polymer is sulfonated so that styrene and/or conjugated diene is sulfonated. On the other hand, the acrylonitrile units are converted by hydrolysis to amides for modification to a hydrophilic resin. For this reaction, the following reaction conditions are used:

The charging amounts of the polymer and the sulfonating agents are preferably such that the total weight of inorganic acids is twice the polymer weight.

If the amount of addition of the sulfonating agent is less than this, the rate of introduction of sulfone groups to styrene or conjugated diene units or the ratio of hydrolysis of acrylonitrile units is lowered thus lowering absorption properties for urine or absorption properties for the ammonia gases.

If the organic solvent is used, the weight of the organic solvent is preferably not more than 200 times the polymer weight. If the amount of addition of the organic solvent is larger than this range, the reaction rate of sulfonation is lowered, while economic demerits are also manifested.

The reaction temperature, which varies significantly depending on whether or not an organic solvent is used, is preferably 0 to 180° C. If the reaction temperature is excessively low, the reaction rate is retarded to raise practical inconvenience. Moreover, it is not possible to produce hydrophilic resins of optimum properties. If the reaction temperature is excessively high, the polymer molecule chains tend to be disrupted by thermal decomposition such that the polymer is readily dissolved in water.

The reaction time of 5 minutes to 40 hours is preferred. If the reaction time is too short, the reaction does not proceed sufficiently. If conversely the reaction time is too long, the production efficiency is worsened.

According to the present invention, the reaction material from the sulfonating processing is rinsed with a large quantity of water and basic aqueous solutions. For rinsing the sulfonation reaction product, a large quantity of water or the basic aqueous solution is added to the reaction material. Alternatively, the reaction material is filtered from the reaction system and a large quantity of water or the basic aqueous solution is added to the filtered material.

Among the basic materials used for the basic aqueous solutions, there are oxides, hydroxides, carbonates, acetates, sulfates or phosphates of alkali metals, such as sodium, lithium or potassium, or alkali earth metals, such as for magnesium or calcium.

For improving smell extinguishing effects of the hydrophilic resins, it is preferred to effectuate only rinsing with water without effectuating neutralization.

The resin produced in this manner is gelated and is subsequently dried by solar drying, heating, depressurization, centrifugation or pressing to produce the desired hydrophilic resin.

The produced hydrophilic resin displays superior smell extinguishing effects against the smell evolved from urine, mainly ammonia gases, due to content of the inorganic materials, such as sulfone groups, carbon black or titanium oxide, while displaying superior urine absorption rate or quantity and superior water retentivity, due to the content of the amide groups. If the hydrophilic resin contains carbon black, there is raised no problem in connection with discoloration even on absorption of urine. Moreover, since the used-up waste materials can be used as the starting polymer, the natural resources can be exploited efficiently to contribute to maintenance of the global environment.

The amount of addition by weight of the hydrophilic resin to the urine is 1/1 to 1/500 and preferably 1/5 to 1/100 of urine.

EXAMPLES

The present invention is hereinafter explained with reference to specified examples. It is noted that these Examples are merely illustrative and are not intended to limit the invention.

The following polymer was sulfonated to produce a desired hydrophilic resin:
(a) Waste ABS resin material (8 mm cassette tape guard panel, black colored portion); polymer composition, 30 mol % of acrylonitrile, 50 mol % of styrene, 20 mol % of butadiene and 1 mol % of carbon black, based on the weight of resin;
(b) SAN resin (transparent pellets) (40 mol % of acrylonitrile and 60 mol % of styrene);
(c) waste materials of nitrile rubber (waste material of oil-resistant rubber hoses); 70 mol % of rubber component and 30 mol % of acrylonitrile; and
(d) a polystyrene reagent (transparent pellets) not containing acrylonitrile nor rubber components not pigments.

It is noted that the polymer (b) or (d) used was crushed articles not larger than 16 mesh, obtained on crushed by a shredder, while the polymer (a) or (c) used was obtained by freeze drying (not larger than 16 mesh).

Preparation Example 1

To 30 g of concentrated sulfuric acid (96 wt %) was added 1 g of the ABS resin waste material (a) and the resulting article was reacted at 80° for 30 minutes. After end of the reaction, solid materials in the system was filtered off by a glass filter, washed with water and dried by a circulating air drier for two hours at a temperature of 115° C. By this operation, a black-colored solid mass was obtained. The amount of the sulfonic acid groups in the solid mass accounted for 35 mol % of the entire monomer unit.

Preparation Example 2

To 90 g of concentrated sulfuric acid (96 wt %) were added 3.5 g of the SAN resin waste material (b) and the resulting mass was reacted at room temperature for 60 minutes. To the reaction system was then added 0.5 g of fuming sulfuric acid containing 60 wt % of $SO_3$ and the reaction was continued for further 30 minutes. After end of the reaction, the solid mass in the system was filtered, washed with water and dried by a direr for two hours. By the above operation, a transparent solid product was obtained. The sulfonic acid groups in the solid mass accounted for 40 mol % of the entire monomer unit.

Preparation Example 3

To 70 g of cyclohexane were added 3 g of the ABS resin waste material (a) and the resulting mixture was maintained at 30° C. and added to with 4.2 g of sulfuric anhydride dropwise. The resulting system was maintained at a temperature of 50±2° C. and reacted for two hours. The solid mass was filtered, washed with water and dried. By this operation, a black-colored solid mass was obtained. The sulfonic acid groups in the solid mass accounted for 29 mol % of the entire monomer unit.

Preparation Example 4

To 5 g of concentrated sulfuric acid (96 wt %) was added 0.2 g of the nitrile rubber and the resulting mixture was reacted at 90° C. for one hour. After end of the reaction, a solid mass was taken out, washed with water and dried. By this operation, a black-colored solid mass was obtained. The amount of the sulfonic acid groups in the solid mass was 45 mol % of the entire monomer unit.

Comparative Example of Preparation 1

A black-colored solid mass was produced in the same way as in Preparation Example 1 except using the reaction temperature of 0° C. and the reaction time of 5 minutes. The amount of the sulfonic acid groups in the solid mass was 1.5 mol % of the entire monomer unit.

Comparative Example of Preparation 2

A black-colored solid mass was produced in the same way as in Preparation Example 1 except using polystyrene (d). The amount of the sulfonic acid groups in the solid mass was 0.4 mol % of the entire monomer unit.

The samples obtained as above (preparation Examples 1 to 4), Comparative Examples of Preparation 1 and 2 and known absorptive resins, namely a cross-linked polyacrylate based hygroscopic resin (powdered product) as a comparative article 3 and a cross-linked polyvinyl alcohol based hygroscopic resin (powdered product 4) as a comparative article 4 were used a urine absorber.

Of the above samples (Preparation Examples 1 to 4, Comparative Examples of Preparation 1 and 2 and comparative products 3 and 4), the properties as the urine absorber were evaluated by the following method:

Utilization Example 1
Utilization Example as a Portable Toilet 20 gs of the respective samples were charged into 15 cm by 20 cm polyethylene bags into each of which 500 cc of urine was added. The statuses of the urine absorbing gels after lapse of one minute were checked.

The samples of the Preparation Examples 1 to 4 absorbed the urine completely so that, if the bags were pressed by hand, no urine was expelled from the gels. It was found that, as the bags charged with the gels were brought to close to the tester's nose, the smell proper to the urine (ammoniac smell) was softened.

In particular, with the samples of the Preparation Examples 1 and 3, a substantially smell-less level was achieved.

The Comparative Examples of preparation 1 and 2 scarcely absorbed urine while scarcely exhibiting smell extinguishing effects.

With the Comparative product 3, the urine was barely absorbed, however, as the polyethylene bag was pressed with hand, the urine was expelled (leaked out) from the gel. It was also found that, as the bags charged with the gels were brought to close to the tester's nose, the smell proper to the urine (ammoniac smell) was felt strongly.

With the Comparative Product 4, the urine was not absorbed completely in one minute, while strong smell proper to the urine was also left.

Utilization Example 2
Utilization Example as Pet Carrier Toilet

A thin sanitary cotton sheet was laid on a 40 cm by 40 cm polyethylene sheet. 60 gs of the respective samples were evenly distributed thereon and a gauze was placed thereon. The resulting layered products, thus produced, were sewed 5 cm by 5 cm to give kilting sheets which were then laid on a pet carrying casing. 1 lit of the urine was allowed to be absorbed in three separate charges.

With the use of the Preparation Examples 1 to 4, the urine was absorbed in its entirety in the portions of the kilting sheet containing the samples without leaking out into the carrying case that can be disposed of as a solid article. On sniffing, the smell proper to the urine was softened.

The results with the Comparative Examples of Preparation were the same as those of the Utilization Example 1, that is, the samples of these Examples were inferior to those of the Preparation Examples 1 to 4 in urine absorption properties, smell extinguishing properties or absorption stability.

What is claimed is:

1. A method for preparing a urine absorber comprising:
   sulfonating a polymer containing sulfonic acid groups and/or sulfonate groups in an amount corresponding to 2 to 95 mol % of entire constituent units by a sulfonizing agent to give a sulfonated reaction mass and
   washing and drying said sulfonated reaction mass to give a hydrophilic resin.

2. A method for absorbing urine characterized in that
   a urine absorber made up of a polymer and 2 to 95 mol % based on the entire constituent units of sulfonic acid groups and/or sulfonate groups in the polymer is contacted with urine to absorb the urine.

* * * * *